United States Patent
Riccio

(10) Patent No.: US 9,895,392 B2
(45) Date of Patent: Feb. 20, 2018

(54) SACCHARIDE FRACTION FROM WHEAT, ISOLATION PROCESS AND FIELD OF USE OF THE INVENTION

(71) Applicant: FARMACEUTICI DAMOR S.P.A., Naples (IT)

(72) Inventor: Rodolfo Riccio, Naples (IT)

(73) Assignee: FARMACEUTICI DAMOR S.P.A., Naples (IT)

( * ) Notice: Subject to any disclaimer, the term of this patent is extended or adjusted under 35 U.S.C. 154(b) by 500 days.

(21) Appl. No.: 14/405,082

(22) PCT Filed: Jun. 4, 2013

(86) PCT No.: PCT/EP2013/061461
§ 371 (c)(1),
(2) Date: Dec. 2, 2014

(87) PCT Pub. No.: WO2013/182551
PCT Pub. Date: Dec. 12, 2013

(65) Prior Publication Data
US 2015/0148309 A1 May 28, 2015

(30) Foreign Application Priority Data

Jun. 4, 2012 (IT) .................. FI2012A0104

(51) Int. Cl.
| | |
|---|---|
| A61K 31/716 | (2006.01) |
| A61K 36/899 | (2006.01) |
| A61K 31/718 | (2006.01) |
| C08B 30/04 | (2006.01) |
| C08L 3/02 | (2006.01) |
| A61K 31/7004 | (2006.01) |
| A61K 31/702 | (2006.01) |
| C12P 19/04 | (2006.01) |

(52) U.S. Cl.
CPC .......... *A61K 31/716* (2013.01); *A61K 31/702* (2013.01); *A61K 31/7004* (2013.01); *A61K 31/718* (2013.01); *A61K 36/899* (2013.01); *C08B 30/046* (2013.01); *C08L 3/02* (2013.01); *C12P 19/04* (2013.01)

(58) Field of Classification Search
None
See application file for complete search history.

(56) References Cited

U.S. PATENT DOCUMENTS 3,812,252 A    5/1974  Silvetti
4,424,213 A *  1/1984  Magee ................ A01N 47/24
                                                        514/186

FOREIGN PATENT DOCUMENTS

| DE | 4123714 A1 * | 1/1992 |
| EP | 0743323 A1 | 11/1996 |
| GB | 1418910 A | 12/1975 |
| JP | H05178750 A | 7/1993 |

OTHER PUBLICATIONS

International Search Report from PCT/EP2013/061461 dated Aug. 6, 2013 (3 pages).
D'Agostino L. et al., "A fraction purified from Triticum vulgare has trophic effects on Caco-2," Gastroenterology, Elsevier, Philadelphia, PA, vol. 104, No. 4, p. a819 (Jan. 1, 1993).
Fiore L. et al., "Differential activities of Triticum vulgare extract and its fractions in mouse fibroblasts," Acta. Therapeutica, vol. 19, No. 2, pp. 151-162 (1993).

* cited by examiner

*Primary Examiner* — Susan Hoffman
(74) *Attorney, Agent, or Firm* — Abelman, Frayne & Schwab

(57) ABSTRACT

Fractions extracted from wheat seeds germinated and macerated in water having a molecular weight comprised between 3 and 30 K Daltons are described.

3 Claims, 1 Drawing Sheet

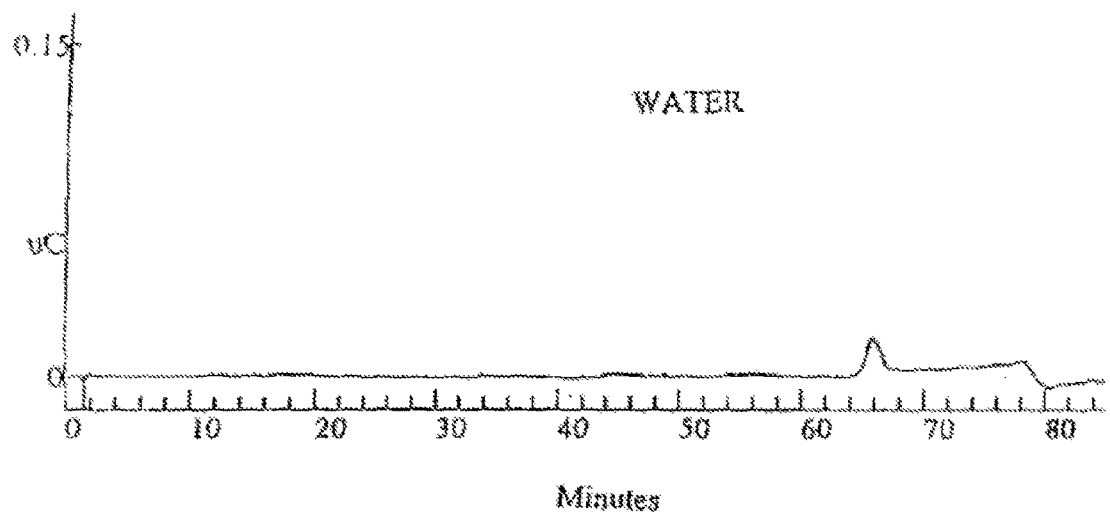
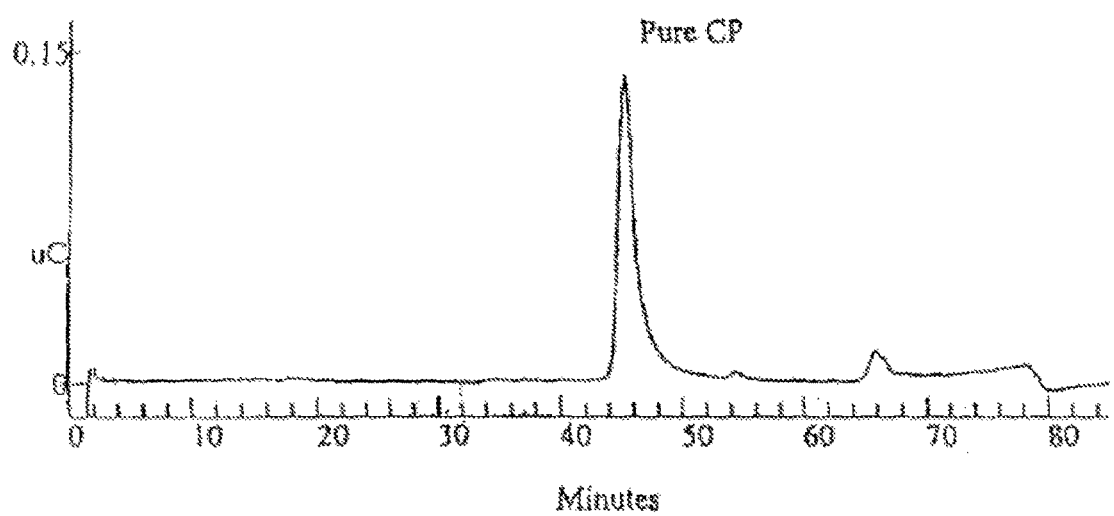
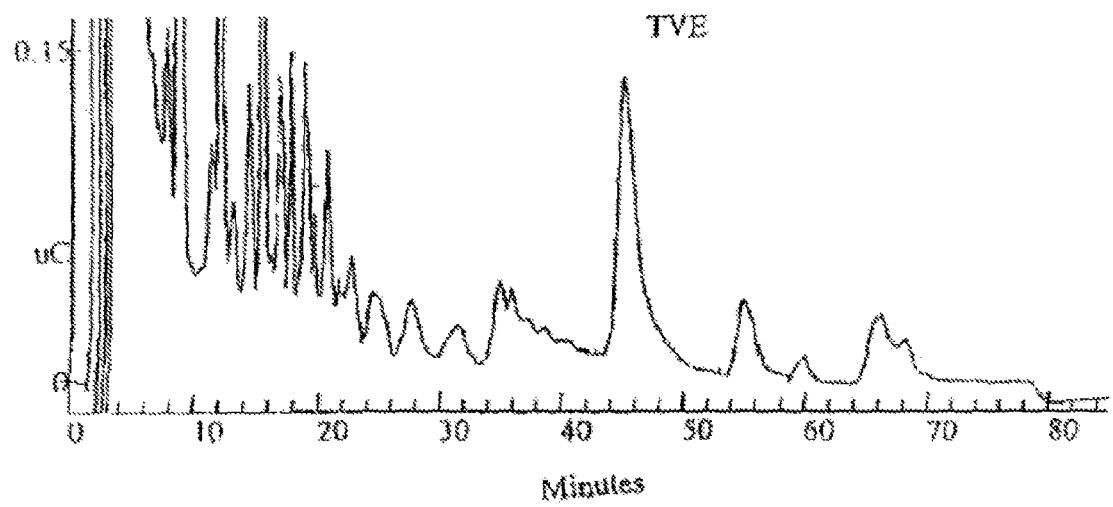

SACCHARIDE FRACTION FROM WHEAT, ISOLATION PROCESS AND FIELD OF USE OF THE INVENTION

CROSS REFERENCE TO RELATED APPLICATION

This application is a national phase of Application No. PCT/EP2013/061461 filed Jun. 4, 2013, and claims priority from Italian Patent Application No. FI2012A000104 filed Jun. 4, 2012, both incorporated by reference in their entirety.

FIELD OF THE INVENTION

The invention relates to the field of natural extracts, in particular extracts from cereals, and to the processes for their isolation.

PRIOR ART

The clinical and cosmetic use of macromolecules of the protein type (such as e.g. the growth factors) or of the glycine type (such as e.g. hyaluronic acid, not treated starch or hydrolysed starch and fractions thereof, other GAGs, glycosaminoglycans, etc), as well as the chemically undefined extracts obtained from various plants (for example Aloe vera, Centellaasiatica, etc) have now become widespread, these products being widely used for example in diseases involving the epidermal tissue (for example wounds or ulcers) or for cosmetic purposes.

In EP 743 323 (in the name of the same Applicants), for example, saccharide fractions obtained from starch are described.

In a few studies, see, for example, D'Agostino et al. "A fraction purified from Triticumvulgare has trophic effects on CaCO-2" [GASTROENTEROLOGY, ELSEVIER, PHILADELPHIA, vol. 104, n° 4, Suppl, 1 Jan. 1993, pp. 819] and in Fiore et al. "Differential activities of Triticumvulgare extract and its fractions in mouse fibroblasts" [ACTA THERAPEUTICA Vol. 19, n° 2, 1993 pages 151-162], saccharide fractions are described that are obtained without specifying the method used for germinating and growing the plants and also containing a peptide fraction, hexose and hexosamine.

These extracts are used as stimulating agents of the re-epithelialisation phase and thus of scar formation, such as soothing agents in cases of skin irritation, for example emollients, and generically in all non-infective disorders of the skin and mucosae.

Search is still directed to the isolation of new compounds of the above-mentioned type, both to widen the availability of products used for the above-mentioned purposes, and to isolate compounds with increased activity, and to obtain products without excessive costs such as, for example, the growth factors and a number of the glucose materials indicated above.

However, as already said, all the natural extracts described above (including wheat extracts) consist of an indeterminate and elevated number of substances of various types and/or of macromolecules, the majority of which have not been identified; and yet it is not always possible to attribute the activity to any of the identified components.

This is also why the means for obtaining vegetable material and the fractions that may optionally be purified therefrom have not been fully described in standardised manner.

Conversely, and surprisingly, the fraction which is the subject of the present invention—as well as being identified and chemically characterised, exhibits all the activities of the total extract and thus represents the principal which is responsible for the action of the total extract.

BRIEF DESCRIPTION OF THE DRAWINGS

FIG. 1 represents the chromatograms obtained by analysing respectively a reference blank (water), the fraction according to the invention (labelled in the drawing as the CP fraction), and the fraction from which the fraction obtained in paragraph (d) of the process according to the invention is separated, designated TVE in the drawing.

SUMMARY OF THE INVENTION

Fractions extracted from germs of wheat macerated in water are described, which fractions have a molecular weight within the range 3 to 30 kDalton.

DETAILED DESCRIPTION OF THE INVENTION

The present invention relates to a fraction of an extract obtained from germs of wheat macerated in water which has a number of biological features typical of growth factors, except that it is obviously of vegetable as well as animal origin, and has the chemical structure of a polysaccharide, not of a protein; said totally unexpected characteristics render this fraction especially interesting for the preparation of drugs and of products useful for the treatment of wounds and ulcers.

More in particular, the present invention relates to a fraction obtained from seeds of germinated wheat, under conditions normally used to obtain analogous extracts that are already known, as described above in what is said about the prior art, having a molecular weight within the range from 3 to 30 kDalton.

It should be borne in mind that the fraction according to the invention is absent in ungerminated seeds, and that only—or principally—this fraction (i.e. that within the range from 3-30 kDalton) has the properties described above.

According to the present invention, the process provides for the preparation of a raw extract obtained from germinated wheat according to known methods, and the subsequent purification of the active fraction.

The above-mentioned process comprises the following steps:

a) germination of wheat seeds, under any conditions of light (preferably in the dark), humidity (preferably at a humidity over 60%), temperature (preferably at 5-20° C.), yielding shoots preferably grown to 3-15 cm in height, in water and/or on inert natural or artificial growth supports;

b) heating of the vegetable material obtained (optionally preventively crushed to small sizes, and with water added) at a temperature within the range 85-125° C., optionally with addition of water, to prepare the next step and to prevent microbial growth;

c) maceration of the material obtained, which is placed in water (preferably at pH 2-4) and optionally left to macerate at low temperatures (10° C. maximum);

d) elimination of the solid residue by means of filtration, pressing or pressing, or by means of other equivalent systems such as extractors, to obtain a first clear solution (understood as a raw extract) which may be sterilised;

e) purification of the fraction with molecular weight between 3,000 and 30,000 daltons from the above-mentioned solution, to thus give a second solution having an elevated percentage content of active fraction f) isolation of the purified active fraction, characterised by molecular weight within the range 3,000 to 30,000 from the above-mentioned second solution if necessary, the seeds may be moistened with purified water before step a).

Step b) and the sterilisation mentioned in step d) are carried out in accordance with conventional techniques, preferably in an autoclave.

Step c) is preferably carried out at a pH between 2 and 4, preferably for 1-72 hours.

Step c) and the elimination of the solid residue in step d) may be carried out with a process of curling. In this case the solution obtained in step d) is added instead of the water of step c) to new seedlings germinated according to step b), and steps c-d are repeated. In this way it is possible to obtain more elevated yields.

The elimination of the fractions with molecular weight below 3000 and above 30,000 (step e) may be carried out by conventional methods known to an expert in the art, for example by means of gel filtration or ultrafiltration.

By analogy, the fraction of interest is isolated by means of the above-mentioned techniques.

The molecular weights mentioned so far are intended to refer to the ultrafiltration membranes used for purifying the fraction which is the subject of the present invention: such values refer to globular proteins, and are therefore to be considered merely indicative of the true molecular weight of the fractions separated therefrom: all the more reason to select the fraction under discussion, which is of the saccharide type and has a linear and branched structure, thus anything but globular.

In its final form, the fraction which is the subject of the present invention may be dried or lyophilised using conventional methods, or preferably left in aqueous solution at a known and pre-established concentration; optionally with addition of a preservative and/or sterilised.

The process generically described above will be more clearly illustrated by the following specific example:

Example

1. Germination 5 kg of moistened wood cellulose is distributed into a series of suitable steel tanks; onto this, 2.4 kg of wheat seeds previously whetted with water is then distributed; the seeds are allowed to germinate in the dark for a few days (4-10 days) in an air-conditioned chamber until seedlings 5-15 cm in height are obtained. During growth, the support is moistened daily by adding a sufficient quantity of water.

The temperature of the chamber is maintained within the range 5-20° C.; and the relative humidity is ≥60%

2. Heating

The contents of the tanks is placed in suitable, hermetically sealed containers, and then autoclaved for 1 hour at 1 atmosphere (≈121° C.)

3. Maceration and Extraction

The material is then transferred into a steel container of suitable capacity, and 100 l of purified water containing 120 ml of 10% v/v sulphuric acid and 60 ml of 10% v/v hydrochloric acid is added. The maceration may proceed for 1-72 hours. The aqueous phase is then extracted under pressure at 300 atmospheres, and the exhausted solid-phase is eliminated.

The liquid thus obtained (defined as "$1^{st}$ pressing) Is supplemented with 120 ml 10% v/v sulphuric acid and 60 ml 10% v/v hydrochloric acid, and mixed with the contents of a further equivalent number of other tanks. The procedure described as "$1^{st}$ pressing" Is then repeated, thus obtaining the "$2^{nd}$ pressing").

The same operations are repeated again, thus obtaining the "$3^{rd}$ pressing" and the "$4^{th}$ pressing".

When placed in contact with the vegetable material to obtain the extraction, the liquid phase is mixed energetically and then kept in a cold place (5-9° C.) for about 24-72 hours.

The final liquid also may be kept in a cold place (5-9° C.) for approximately 24- to 72 hours.

4. Filtration and Sterilisation

The liquid from the $4^{th}$ pressing Is filtered by conventional methods; in suitable containers, it is then autoclaved by applying a cycle equivalent to 1 hour at 1 atmosphere.

5. Ultrafiltration

Using suitable ultrafiltration instrumentation with cartridges having a cut-off of 3 kdaltons, the liquid obtained above is ultrafiltered to the maximum permitted by the instrumentation; water is added to the retained liquid, and the ultrafiltration is repeated 2-3 times to discard the lower molecular weights contained in the eluted phase.

Then, using the same method but substituting the cartridges with others having a cut-off of 30 kdaltons, the residue containing the molecular weights above 3,000 daltons is further ultrafiltered: however, in this case the retained residue represents the molecular weights greater than 30,000 kdaltons and is discarded, while the eluted phase contains the active fraction having molecular weights within the range 3,000 to 30,000 daltons.

The solution containing the active fraction is then lyophilised (or exsiccated) as it is or on a suitable support; or it is sterilised (as it is, with the addition of a preservative, for example 2% w/w phenoxyethanol).

A. Chemical Data Relating to the Active Fraction

1. Chromatographic Analysis of the Fraction

An HPAE (High-Pressure Anion Exchange) chromatographic system was selected, coupled with a PAD detector (Pulsed Amperometric Detector), especially indicated for carbohydrate analysis.

The chromatographic system has the following features:
System of Pumps with Linear Elution Having a Binary Gradient
Eluent 1: 0.5M NaOH
Eluent 2: 1M sodium acetate in 0.5M NaOH The gradient is imposed by the following linear program (with constant flow equal to 1.0 ml/min), where % 2 indicates the percentage of the eluent relative to pump 2 with respect to the total mixture:

| PROGRAMME OF GRADIENT | | |
|---|---|---|
| STEP | TIME | % eluent 2 |
| 0 | 0.0 | 5 |
| 1 | 0.1 | 5 |

-continued

PROGRAMME OF GRADIENT

| STEP | TIME | % eluent 2 |
|---|---|---|
| 2 | 5.0 | 5 |
| 3 | 15.0 | 15 |
| 4 | 30.0 | 15 |
| 5 | 30.1 | 20 |
| 6 | 40.1 | 20 |
| 7 | 40.2 | 30 |
| 8 | 50.2 | 30 |
| 9 | 50.3 | 35 |
| 10 | 60.3 | 35 |
| 11 | 75.0 | 100 |
| 12 | 76.0 | 5 |
| 13 | 85.0 | 5 |

Chromatographic Column

Carbopac PA1 (4×250 mm) with Carbopac PA1 Guard pre-column (10-32) or equivalent, maintained at a temperature of 35° C.

PAD detector fitted with a gold electrode, under the following operating conditions:

Indicative detection programme

| Time (sec) | E (volt) |
|---|---|
| 0.00 | +0.10 |
| 0.20 | +0.10 start of integration |
| 0.40 | +0.10 end of integration |
| 0.41 | −2.00 |
| 0.42 | −2.00 |
| 0.43 | +0.60 |
| 0.44 | −0.10 |
| 0.50 | −0.10 |

*Preparation of the Standard Solution

A series of active fraction solutions having concentrations within the range 4 to 12 mg in 100 ml of deionised water is prepared on the basis of a concentrated solution of pure ACTIVE fraction, to be understood as the reference standard; or alternatively using a working standard calibrated against a reference standard.

*Procedure

100 µl is injected as the blank, verifying that the related chromatogram is planar with the exclusion of a few peaks due to the jumps in gradient of the eluent system.

100 µl of each of the test solutions is then injected.

The chromatogram of the sample of purified active fraction has a single peak with Rt≈44 minutes, corresponding precisely to the active fraction (see FIG. 1, sample labelled "CP fraction").

The chromatogram of the sample of purified or partially purified extract shows a characteristic course with a series of peaks, among which the peak with Rt≈44 minutes is the one relating to the active fraction.

2. Chromatographic Analysis of the Fraction Following Hydrolysis

This control check is performed to verify the nature of the individual monosaccharides constituting the oligosaccharide structure of the test fraction.

HPA (high-performance and ion exchange) chromatography is used on a hydrolysed sample.

The type of instrumentation is equivalent to that mentioned above for checking the intact, that is the non-hydrolysed, fraction.

Procedure

The hydrolysis is performed by adding 0.35% (v/v) HCl to the fraction and hydrolysing at 100° for 20 hours, on a sample at an active-fraction concentration within the range 5-75 mg/100 ml.

The HPA analytical conditions are the following:
Carbopack PA1, 4×250 mm column
Isocratic eluent 0.017 N NaOH
Constant flow at 1 ml/min
PED detection
Injection volume: 75 µl of the solution of hydrolysed sample, diluted 1 to 100 with water.

Equivalent analysis is performed using the more common monosaccharides as the standard.

The sample under investigation proved to have a massive and predominant presence of glucose, wherein other peaks (relating to other monosaccharides or similar: mannose, galactose, glucosamine, pentose etc) are absent or present only in traces.

An identical analysis performed prior to hydrolysis analogously yields the absence of any monosaccharides, demonstrating that the fraction consists of an oligosaccharide structure.

B. Biological Activity of the Fraction

The fraction according to the present invention has proved to possess in vivo pronounced re-epithelialising and curative activity of wounds and/or ulcers of any type, similar to that of growth factors of animal origin, and therefore it can be used in medicinal-product production for treating wounds and ulcers.

It also shows, in vitro, considerable activation of cell growth in fibroblasts and of ODC activity.

Activation of the mechanism of inositol phospholipid hydrolysis, which is typical of growth factors, has also been demonstrated.

The therapeutic activity is illustrated in what follows by various pharmacological studies.

1. Test of Stimulation of Fibroblast Cell Growth

Fibroblasts are cells which play a fundamental role in the mechanism of tissue repair. The test is therefore performed to verify whether the curative effect of the product is observed as the result of a mechanism of cell growth stimulation of these organisms.

Procedure

Cultures of 3T3 mouse fibroblasts are kept in a DMV medium supplemented with 10% v/v calf serum (CS), penicillin (10 U/ml). These cultures are cultivated in 25-ml Falcon bottles at 37° C. in a humid atmosphere containing 5% CO2 and subculture every 4-6 days. The confluent cultures are therefore washed with 3 ml PBS and are trypsinised with 0.25% trypsin at 37° C. To deactivate the trypsin, 2 ml DME is added and the cellular pellet obtained after centrifugation is diluted with fresh culture medium until a density suitable for dissemination is reached.

The stimulant effect of the palate is tested on fibroblasts that have been left in a quiescent state in a medium containing low concentrations of CS. The cells are seeded at a density of approximately 2000-4000 cells per plate in DME supplemented with 5% CS. The medium is renewed after 18 hours and replaced with fresh medium containing 0.6% CS, and the cells are left to grow for another 48 hours before each successive activity test. For the test in question, the product (diluted in water at a concentration of 20 mg/100 ml) is added each day in increasing concentrations between 2 and 20% v/v throughout the growth period.

At the end of the fifth day, the number of cells is stimulated by trypsinising the cultures and counting the cells in a Coulter counter.

Results

Addition of the product at the dilution indicated produces a marked, dose-dependent stimulation of cell growth. The effect begins to be significant in a percentage of 5% of the product (diluted as indicated above), and is maximal between 10 and 20%, in a quantity slightly lower than that exhibited by CS for parity of concentration, but at least four times greater than that of a control, in the maximum point.

2. Test of ODC (Ornithine Decarboxylase) Activation

Ornithine decarboxylase is the key enzyme in the synthesis of spermidene-polyamine, catalysing the conversion of ornithine amino acid intoputrescine. These polyamines are co-involved in controlling the processes of cell multiplication. The test is conducted by verifying whether the action-stimulating the growth of fibroblasts produced correlates with an increase in ODC activity.

Procedure

The activity of ODC is tested in 3T3 cells grown in a medium containing 0.6% CS (calf serum) and is prepared as described above in the fibroblast growth stimulation test.

The ODC activity is measured using the method described by Russell [Proc. Natl. Acad. Sci. USA 60 1420 (1968)], 6 hours after addition of the product (diluted in water at the concentration of 20 mg/100 ml), in increasing quantities from 1% to 10% v/v Results At the concentrations and under the conditions tested, the product shows—6 h after the addition and dose-dependently—a notable stimulation of ODC of approximately 4 times greater than that of a control, and similar to that of CS for parity of concentration.

3. Test of the Stimulation of Inositol-Phospholipid Hydrolysis

It is a widely documented that one of the principal biochemical mechanisms with which a substance is capable of activating the processes responsible for the activation and for cell multiplication consists in the specific stimulation of hydrolysis of the membrane inositol phospholipids, which in turn produce an increase into second messengers, inositol triphosphate (InsP3) and diacylglycerol. This mechanism is intimately connected with, inter alia, another system of signal transduction, the activation of tyrosine kinase responsible, for example, for the action of EGF (epidermal growth factor), of insulin and of insulin-like factors.

It is therefore considered advantageous to evaluate the effect of the product on the accumulation of inositol phosphate (as a specific index of phosphoinositide hydrolysis) in 3T3 cells, both under baseline conditions and after stimulation with CS serum, which is known to be an activator of the metabolism of phospholipids in fibroblasts.

Procedure

The hydrolysis of inositol phospholipids is tested in 3T3 cells grown in a medium containing 0.6% CS (calf serum), and prepared as described above in the test of stimulation of fibroblast growth.

Once quiescence is attained, the cells are washed with a Ham F-10 medium (with low concentration of inositol), and incubated at 37° C. for 24 hours with the addition of 0.6% CS and 0.6 µmol of 2-[3H] myoinositol for 24 hours, to label the membrane inositol phospholipids. At the end of this incubation, the cells are washed with Krebs-Henseleit buffer containing 10 mmolLiCl and 0.1% BSA. The cells are then incubated for 24 hours with increasing amounts from 0 to 20% (v/v) of the product (in aqueous solution at a concentration of 4 mg/100 ml), with and without 10% CS.

The inositol phosphates are then measured out using the following technique: the incubation medium is aspirated away, and the cells are extracted with chloroform/methanol/water 1/1/1 (v/v), following centrifugation, the aqueous phase is taken and charged onto 1 ml of Dowex-1 columns in formiate form, the columns are washed with 24 ml of water to remove the labelled inositol which has not been incorporated; the inositol phosphates are then eluted by washing with 0.2 m ammonium formiate and 0.1 M formic acid. The radioactivity is then determined by scintillation spectrometry.

Results

At the concentrations and under the conditions tested, the product shows marked and dose-dependent stimulation of the hydrolysis of the inositol phospholipids, approximately 4 times greater than that of a control, and similar to that of the CS concentration equivalent. It should be noted that the simultaneous presence of the product and of CS leads to a greater activation than with CS alone (and with the product alone), suggesting that there is an advantageous synergistic effects between the two components.

4. Test of Healing In Vivo on Experimental Wounds

The test of healing in vivo, performed on animals by topical application, demonstrates the efficacy of the product in the treatment of wounds.

Procedure

The test is performed on male rats of the Wistar strain weighing within the range 220 to 250 g. For one week before the test, the animals are kept in controlled conditions of temperature, humidity and light, with free access to food and water. The animals are subdivided into homogenous experimental groups comprising 10 animals each; one group is used as the control and is treated with a placebo, the other group is treated with the product.

On the morning of the first day of the test, all the animals are subjected to a surgical procedure to produce a standard wound, obtained in the following way: following mild anaesthesia (10% ethyl urethane at a dose of 10 ml/kg), the door so lumbar region of each animal is accurately shaved, after being disinfected, the skin is cut around the edge of a metal disc of 2.5 cm diameter, 8.5 in the case of a topical treatment, and the skin and subcutaneous tissue is then removed using curved forceps. Substantially identical wounds are obtained in all the animals.

After each day of treatment, the wound is suitably covered, and the animals are kept in individual cages.

The extent of the wound is measured with a planimeter (tracing the wound on a sheet of transparent paper) every day for 9 days (5 days in the case of topical treatment).

Daily Treatment Using Topical Application

The wounds of the animals of the control group are treated with sterile gauze impregnated with placebo, consisting of a physiological solution (0.9% NaCl).

The wounds of the animals in the other group treated with sterile gauze impregnated with the product, dissolved in water at a concentration of 20 mg/100 ml.

Results

In the animals treated with the product, an acceleration of the repair process is observed, manifested with a notable reduction in the wound areas as compared with the control group, on average of around 20-30% at the end of the treatment.

Preparation of Pharmaceutical and/or Cosmetic Products

The active fraction which is the subject of the present invention may be used to prepare products having pharmaceutical or cosmetic activity.

The dose may vary according to the pathology and the type of tissue to be treated, the degree of extension, the patient parameters (age, sex, weight), and the type of pharmaceutical or cosmetic composition. The active fraction dosage may vary, also as a function of the degree of purification of the fraction used.

The fraction which is the subject of the present invention may be administered in the form of compositions containing an effective quantity of the said fraction mixed with excipients and conventional carrier substances known to the person skilled in the art.

The compositions of the present invention may be prepared using known methods and conventional techniques.

Other active components may be present in the final preparation.

By way of example of pharmaceutical and cosmetic compositions, there are vials, lotions, creams, ointments, gels, solutions, medications, suppositories, ovules, soaps, foams, tablets, powders, milks.

The invention claimed is:

1. A process for obtaining a fraction obtained from germinated wheat seedlings useful in treating non-infective disorders of skin and mucosa, having a molecular weight of from 3,000 to 30,000 daltons, comprising:

(i) germinating wheat seeds in darkness, in water or on a support at humidity above 60% relative humidity, and at a temperature of from 5-20° C. for from 4-10 days, to form wheat seedlings;

(ii) treating said wheat seedlings at 85-120° C., for from 25-120 minutes, (iii) macerating the heat treated wheat seedlings of (ii) at a temperature of from 2-10° C., at a pH of from 2 to 4;

(iv) separating solid residue from aqueous solution to obtain a clear solution;

(v) sterilizing said clear solution, and (vi) separating a fraction of said clear solution which contains components from said germinated wheat seedlings having molecular weights of from 3,000 to 30,000 daltons.

2. The process of claim 1, comprising adding water in step (ii).

3. The process of claim 1, comprising separating said solid residue from said aqueous solution with a synthetic membrane, a paper filter, or a press.

* * * * *